United States Patent [19]

Gruber

[11] 3,968,092

[45] July 6, 1976

[54] USE OF AROMATIC FURFURYL POLYCARBAMATES AS CHLOROPRENE POLYMER VULCANIZATION ACCELERATORS

[75] Inventor: Wilhelm Franz Gruber, Wilmington, Del.

[73] Assignee: E. I. Du Pont de Nemours and Company, Wilmington, Del.

[22] Filed: Mar. 5, 1975

[21] Appl. No.: 555,432

Related U.S. Application Data

[63] Continuation of Ser. No. 452,337, March 18, 1974, abandoned.

[52] U.S. Cl. .......................... 526/17; 260/77.5 CR; 260/77.5 AT; 260/77.5 TB; 526/26; 526/49; 526/89; 526/220; 526/295
[51] Int. Cl.² ............... C08F 214/00; C08F 136/16; C08F 218/00; C08F 18/24
[58] Field of Search .... 260/92.3, 77.5 AT, 77.5 TB, 260/77.5 CR, 77.5 AM, 77.5 MA, 87.5 R, 784

[56] References Cited
UNITED STATES PATENTS 3,509,103  4/1970  Teague et al. ............... 260/77.5 TB
3,793,252  2/1974  Corish et al. ................. 260/77.5 CR

FOREIGN PATENTS OR APPLICATIONS 909,267  4/1959  United Kingdom ............... 260/92.3

OTHER PUBLICATIONS

"Neoprenes," Murray & Thompson 1963, Du Pont de Nemours & Comp., Chapter III (pp. 21–25).

*Primary Examiner*—Joseph L. Schofer
*Assistant Examiner*—Herbert J. Lilling

[57] ABSTRACT

Polycarbamates derived from furfuryl alcohol and certain aromatic di- and polyisocyanates are effective vulcanization accelerators for chloroprene polymers, while at the same time conferring on the polymer compounds exceptional processing safety. These polycarbamates also are virtually nontoxic to experimental animals. Vulcanization of chloroprene polymers is accomplished in the presence of magnesium and zinc oxides, both of which must be present.

14 Claims, No Drawings

USE OF AROMATIC FURFURYL POLYCARBAMATES AS CHLOROPRENE POLYMER VULCANIZATION ACCELERATORS

This is a continuation of application Ser. No. 452,337, filed March 18, 1974, and now abandoned.

BACKGROUND OF THE INVENTION

This invention relates to certain novel polycarbamates derived from furfuryl alcohol and aromatic polyisocyanates, the polycarbamates being useful as vulcanization accelerators for chloroprene polymers.

Homopolymers and copolymers of chloroprene are important commercial elastomers. These elastomers can be cured in the presence of certain metal oxides, such as zinc or magnesium oxides, at elevated temperatures. Curing is accelerated by a number of organic compounds, such as thioureas or derivatives of dithiocarbamic acid, which also improve the properties of the vulcanizates. Accelerators are often necessary, especially in the case of chloroprene polymers prepared in the presence of alkyl mercaptans or dialkyl xanthogen disulfides. Most commercially available accelerators produce excellent cures; yet, the accelerators must also satisfy other requirements, especially that of good processing safety of compounded elastomers. Another important requirement is handling safety, that is, freedom from serious toxicological hazards.

For these reasons, new chemical substances continue to be made and tested as possible polychloroprene vulcanization accelerators.

SUMMARY OF THE INVENTION

According to this invention, it has now been found that a class of novel polycarbamates is useful as effective and virtually non-toxic vulcanization accelerators for chloroprene polymers. For the purpose of the present disclosure, the term "chloroprene polymer" means not only homopolymers of chloroprene but also copolymers with at least one other monomer, provided that chloroprene constitutes at least 40 weight percent of the resulting copolymer.

The accelerators of the present invention can be represented by the following formula

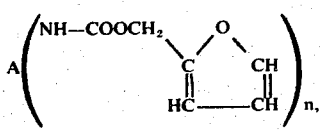

wherein $n$ is a positive number from 2 to 3, and A is an aromatic radical selected from 1,3-phenylene, 1,4-phenylene, 4,4'-methylenediphenylene, and polymethylene polyphenyl having a functionality of up to about 3.

The aromatic rings can be further substituted with one or more $C_1$–$C_4$ alkyl groups.

DETAILED DESCRIPTION OF THE INVENTION

The accelerators of the present invention are made from furfuryl alcohol and a polyisocyanate, $A(NCO)_n$. Suitable polyisocyanates include 1,3-phenylenediisocyanate, 1,4-phenylenediisocyanate, 4,4'-methylenediphenylenediisocyanate, and polymethylene polyphenyl isocyanate. The last named material is commercially available from the Upjohn Company, Kalamazoo, Mich., under the tradename "PAPI". Its functionality, $n$, usually is greater than 2, often in the 2.3–2.7 range.

The reaction of furfuryl alcohol with polyisocyanate normally is carried out using approximately stoichiometric proportions or a molar excess of the furfuryl alcohol in a solvent which is inert to isocyanate groups. Suitable solvents include, for example, aliphatic and aromatic hydrocarbons and chlorinated hydrocarbons. The following specific solvents illustrate this class: benzene, toluene, ortho- or meta- dichlorobenzene, hexane, heptane, cyclohexane, chloroform, methylene chloride, trichloroethylene, and carbon tetrachloride.

The reaction temperature is maintained within the range of about 20°–140°C, preferably about 40°C. Below 20°C, the reaction rate is impractically slow. Above 140°C, there is a considerable danger of resinification. U.S. Pat. No. 2,926,157, for example, teaches the preparation of useful resinous products from diisocyanates and furfuryl alcohol at temperatures of 140°–220°C. In the present case, formation of resinous products is undesirable because they are not effective vulcanization accelerators.

In practice, furfuryl alcohol is added gradually with good agitation to a solution of polyisocyanate in the solvent. The reaction then is completed by increasing the temperature, for example, to reflux. Carbamate formation also can be catalyzed in any manner known in the art, for example, by addition of a tertiary amine. The product normally is isolated from the reaction mixture by any convenient technique, such as filtration or evaporation of the solvent. Although the crude product usually is of satisfactory purity, it can be purified by recrystallization.

These polycarbamates are used as vulcanization accelerators at the level of about 0.5–4 parts by weight per 100 parts of chloroprene polymer. Below the lower limit the cure may be unsatisfactory, while amounts above the upper limit usually do not provide any additional advantages and thus are uneconomical.

The chloroprene polymers which can be vulcanized in the presence of metal oxides and polycarbamates of the present invention are, in addition to polychloroprene, copolymers of chloroprene with other copolymerizable monomers such as, for example: styrene, vinyltoluenes, vinylnaphthalenes methyl methacrylate, acrylonitrile, acrylic and methacrylic acids, 1,3-butadiene, isoprene, and 2,3-dichloro-1,3-butadiene. All such polymers are prepared by methods known in the art, for example, as described in U.S. Pat. Nos. 2,494,087; 2,576,009; 2,567,117; 2,426,854; and 2,914,497.

Both magnesium and zinc oxides are present in the compounding recipe. The concentration of magnesium oxide is about 0.5–15 parts by weight, preferably 1–4 parts, per 100 parts of the polymer. Zinc oxide is present at a concentration of about 2–15 parts by weight per 100 parts of the polymer, preferably about 5 parts. Other ingredients such as antioxidants, pigments, fillers, and softening agents can also be incorporated into the polymer prior to the cure.

Vulcanization takes place at about 125°–220°C. during a period of two minutes or less to one hour or more. The accelerators of the present invention are particularly useful for rapid cures at high temperatures, for example, in injection molding machines. However, vulcanization can be accomplished in any convenient type of equipment using any convenient technique. For example, heating can be combined with shaping in a mold under pressure, or shaped articles can be heated with steam, hot air, or a hot liquid.

The polycarbamates of the present invention also are useful as cure accelerators in latices or solvent-based cements.

These polycarbamates are exceptionally safe in that they do not cause premature vulcanization (scorch) during processing. The vulcanizates have physical properties comparable to those of vulcanizates produced using conventional accelerators. These accelerators also are virtually free of toxicological hazards.

One of the carbamates of the present invention, 2,4-toluenedicarbamic acid difurfuryl ester, was administered to pregnant rats at levels of 450–2250 mg/kg and was found to be nontoxic to mothers, not embryolethal, and not teratogenic. Applied as a 50% paste in propylene glycol to shaved intact rabbit skin, it caused no irritation; and applied as a 50% or 25% solution in fat/acetone/dioxane to guinea pig skin, it caused no irritation or sensitization. 2,4-Toluenedicarbamic acid difurfuryl ester was a mild eye irritant but produced no eye damage. The material was for all practical purposes nontoxic when administered by intragastric intubation to young adult male rats in single doses, its $LD_{50}$ being above 10,000 mg/kg.

This invention is now illustrated by the following representative examples in which all parts, proportions, and percentages are by weight unless indicated otherwise.

EXAMPLES

I. Preparation of compounds.

Example 1—2,4-Toluenedicarbamic acid, difurfuryl ester

To a solution of 522 g. (3 moles) of 2,4-toluenediisocyanate in 500 ml. of benzene under a nitrogen atmosphere is added a solution of 588 g. (6 moles) of furfuryl alcohol in 500 ml. of benzene at such a rate as to maintain the temperature below 50°C. The reaction is completed by refluxing for 3 hours (about 80°–90°C.) The reaction mixture is allowed to stand at room temperature overnight, during which time the product diurethane crystallizes. The material is collected by filtration, dried, and pulverized. The yield is 916 g of material (82.5% of theoretical) having a melting point of 154°–156°C.

| Analysis: | Calculated | Found |
|---|---|---|
| C, % | 61.6 | 61.7 |
| H, % | 4.9 | 4.9 |
| N, % | 7.6 | 7.7 |
| M.W. | 370.2 | 377 |

Example 2—Mixture of difurfuryl esters of 2,4-toluenedicarbamic acid and 2,6-toluenedicarbamic acid In this example the isocyanate used as a starting material is a mixture of 80% 2,4-toluenediisocyanate and 20% 2,6-toluenediisocyanate. To a solution of 418 grams (2.4 moles) of the isocyanate in 2000 ml. of dry topped trichloroethylene under a nitrogen atmosphere is added with stirring 500 grams (5.1 moles) of furfuryl alcohol over a 5-minute period. Six drops of N,N-dimethylcyclohexylamine are added as catalyst. In about 1.5 hours the temperature has reached 42°C. The reaction mixture is heated to 60°C. and maintained at that temperature for about 1 hour. The reaction mixture is allowed to stand overnight and the thick white precipitate is worked up by filtration and washing once with hexane. The product is dried overnight at 100°C. in a vacuum oven. The yield is 676 g. (76%) of a white, crystalline solid having a melting range of 149°–158°C. Analysis shows no isocyanate groups. The product is micronized.

| Analysis: | Calculated | Found |
|---|---|---|
| C, % | 61.6 | 61.5 |
| H, % | 4.9 | 4.9 |
| N, % | 7.6 | 7.7 |
| M.W. | 370.2 | 365 |

Example 3—Difurfuryl ester of 4,4'-methylenedicarbanilic acid

This reaction is carried out in substantially the same way as Example 2, except that the isocyanate reactant is 600 g. (2.4 moles) of 4,4'-methylenebis(phenyl isocyanate). The furfuryl alcohol is added over a period of 2 hours. The temperature rises from 23°C. to 40°C. After stirring for another 2 hours, the reaction mixture is heated to 75°–80°C. for 1 hour and allowed to stand overnight. The product is filtered off and dried overnight in a vacuum oven. The yield is 968 g. (90%) of a product melting at 140°–147°C. The isocyanate content is zero. The product is micronized.

| Analysis: | Calculated | Found |
|---|---|---|
| C, % | 67.2 | 67.0 |
| H, % | 4.97 | 4.9 |
| N, % | 6.28 | 6.3 |
| M.W. | 446.20 | 447 |

Example 4 Condensate of polymethylenepolyphenyl polyisocyanates with furfuryl alcohol In this example the polyisocyanate used is a commercial mixture prepared by condensing formaldehyde with aniline in an acid medium using the general method disclosed in U.S. Pat. No. 2,683,730. The mixture has a molecular weight of about 386 and a functionality of about 2.3 to 2.7 (PAPI supplied by Upjohn Co.).

To a solution of 386 grams of polyisocyanate in 400 ml. of benzene under a nitrogen atmosphere is added a solution of 300 g. (3.06 moles) of furfuryl alcohol in 400 ml. of benzene. As a catalyst, 10 drops of N,N-dimethylcyclohexylamine are added. The temperature increases from 25° to 45°. The reaction is completed by refluxing for 15 hours (about 80°–90°C.). The solvent is evaporated, leaving 550 grams (80% yield) of product having a melting range of 70°–90°C. Analysis shows an NCO content of 0.3%. The molecular weight is found to be 780.

II. Testing as vulcanization accelerators for chloroprene polymers

The following chloroprene polymers are used in these examples:

Chloroprene Polymer A. A mercaptan-modified chloroprene polymer prepared by polymerizing chloroprene as described in Example 6 of U.S. Pat. No. 2,494,087.

Chloroprene Polymer B. A chloroprene polymer prepared as described in Example 2 of U.S. Pat. No. 3,655,827, in which the components are blended in a proportion by weight of 78 parts of sol polymer and 22 parts of gel polymer.

Chloroprene Polymer C. A copolymer prepared by copolymerizing 98 parts of chloroprene and 2 parts of 2,3-dichloro-1,3-butadiene in the presence of 0.4 part of sulfur and about 0.4 part of diethyl xanthogen disulfide, substantially as described in Example 1, Sample C, of U.S. Pat. No. 3,766,121.

Testing is carried out by the following methods:

Processing safety is measured by obtaining Mooney scorch data at 121°C. according to ASTM Method D-1646-72 using the small rotor.

Bin storage stability is evaluated by repeating the Mooney scorch test on samples which have been compounded and stored for 2 weeks at 38°C. and noting the change in the minimum viscosity. An increase in the viscosity indicates that cross-linking has occurred.

Tensile properties of the cured samples are obtained by ASTM Method D 412-68.

Maximum cure rate is determined at 153°C. (unless otherwise stated) by means of the Monsanto Oscillating Disc Rheometer (ODR). Curing curves are obtained in which the viscosities (torque in inch-pounds) are plotted against time in minutes. Maximum cure rate is obtained by measuring the slope of the curve at its steepest point. The units are in lb.-inches/minute.

The following abbreviations are used in the tables:
$M_{100}$ — Modulus at 100% elongation, psi
$M_{300}$ — Modulus at 300% elongation, psi
$T_B$ — Tensile strength at break, psi
$E_B$ — Elongation at break, %

Example 5

In this example chloroprene Polymer A is used, and the accelerator is the difurfuryl ester of 2,4-toluenedicarbamic acid of Example 1. Samples of the polymer are compounded using the following recipe:

| | Parts by Weight |
|---|---|
| Chloroprene polymer A | 100 |
| Stearic acid | 0.5 |
| N-Phenyl-1-naphthylamine | 2 |
| Magnesia | 4 |
| Semi-reinforcing furnace black | 58 |
| Naphthenic oil | 10 |
| Zinc oxide | 5 |
| Compound of Example 1 | As Shown |

For comparison, control samples are cured with tetramethylthiourea (TMTU) in approximately equivalent molar amounts. TMTU is a relatively safe processing accelerator compared with the well-known but scorchy 2-mercapto-2-imidazoline.

The results of the tests are shown in the following table.

TABLE I

| Accelerator | Compound of Example 1 | | TMTU | |
|---|---|---|---|---|
| Amount | 1.9 | 3.0 | 0.68 | 1.0 |
| Mooney scorch | | | | |
| Original (Unaged) | | | | |
| Minimum | 17 | 17 | 18 | 19 |
| Minutes to 10-point rise | — | — | 43 | 30 |
| Points rise after 45 min. | 4 | 3 | — | — |
| Aged 2 weeks at 38°C. | | | | |
| Minimum | 20 | 18 | 24 | 27 |
| Minutes to 10-point rise | — | — | 28 | 22 |
| Points rise after 45 min. | 2 | 2 | — | — |
| Tensile properties (cured 25 minutes at 153°C.) | | | | |
| $M_{100}$ | 630 | 550 | 670 | 690 |
| $T_B$ | 2760 | 2830 | 2865 | 2740 |
| $E_B$ | 295 | 305 | 275 | 240 |
| Maximum cure rate (ODR) | 11.1 | 14.8 | 7.7 | 11.9 |

It can be seen that the compound of Example 1 is even safer processing that TMTU, yet provides a good rate of cure. Furthermore, the stocks containing the dicarbamate have excellent bin storage stability, and the vulcanizates have tensile properties comparable with those obtained using the conventional accelerator.

Example 6

Example 5 is repeated except that samples are cured for 20 minutes at 166°C. to show the utility of the compound in a higher temperature cure. The results are shown in Table II.

TABLE II

| Accelerator | Compound of Example 1 | | TMTU | |
|---|---|---|---|---|
| Amount | 1.9 | 3.0 | 0.68 | 1.0 |
| Tensile properties (cured 20 min. at 166°C.) | | | | |
| $M_{100}$ | 520 | 570 | 450 | 610 |
| $T_B$ | 2720 | 2735 | 2705 | 2795 |
| $E_B$ | 305 | 295 | 340 | 255 |
| Maximum Cure Rate (ODR) | 13.2 | 20.6 | 7.8 | 12.8 |

When curing is carried out for 10 minutes at 210°C., the following results are obtained:

TABLE III

| Accelerator, Compound of Example | 1 | 1 | 3 | 3 | 3 |
|---|---|---|---|---|---|
| Amount | 1.9 | 3.0 | 0.95 | 1.9 | 3.0 |
| $M_{100}$ | 560 | 620 | 450 | 510 | 550 |
| $M_{300}$ | 2180 | 2540 | 2170 | 2355 | 2410 |
| $T_B$ | 2815 | 2920 | 2660 | 2750 | 2810 |
| $E_B$ | 370 | 345 | 365 | 350 | 370 |

Example 7

This example is carried out in substantially the same way as Example 5 except that the accelerator is the compound of Example 2 (a mixture of difurfuryl esters of 2,4-toluenedicarbamic acid and 2,6-dicarbamic acid). The results are shown in the following table.

TABLE IV

| Accelerator | Compound of Example 2 | |
|---|---|---|
| Amount | 1.9 | 3.0 |
| Mooney Scorch | | |
| Original (Unaged) | | |
| Minimum | 17 | 17 |
| Points rise after 45 min. | 4 | 3 |
| Aged 2 weeks at 38°C. | | |
| Minimum | 18 | 17.5 |
| Points rise after 45 min. | 2 | 3 |
| Tensile properties | | |
| (Cured 25 min. at 153°C.) | | |
| $M_{100}$ | 570 | 630 |
| $T_B$ | 2950 | 2930 |
| $E_B$ | 320 | 305 |
| Maximum cure rate (ODR) | 10.3 | 13.6 |

Example 8

In this experiment chloroprene Polymer B is used, and the accelerator is the compound of Example 1. The compounding recipe is as follows:

| | Parts by weight |
|---|---|
| Chloroprene Polymer B | 100 |
| Stearic acid | 0.5 |
| N-Phenyl-1-naphthylamine | 2. |
| Semi-reinforcing furnace black | 58 |
| Naphthenic oil | 10 |
| Paraffin | 1 |
| Magnesia | 1 |
| Zinc oxide | 5 |
| Compound of Example 1 | As Shown |

The results are presented in Table V.

TABLE V

| Accelerator, amount | 1.9 | 3.0 | Comparison (a) |
|---|---|---|---|
| Mooney scorch | | | |
| Minimum | 21.5 | 22 | 22.5 |
| Minutes to 10-point rise | 45 | 41 | 19 |
| Tensile properties | | | |
| (cured 30 min. at 153°C.) | | | |
| $M_{300}$ | 2420 | 2460 | 2440 |
| $T_B$ | 2720 | 2920 | 3030 |
| $E_B$ | 345 | 360 | 365 |
| Maximum cure rate (ODR) | 12.2 | 16.7 | 12.0 |

(a) The comparison is made with a conventional curing system consisting of the following:

| | Parts by Weight |
|---|---|
| 2,4-toluenedicarbamic acid, ester with 2-dimethylaminoethanol | 2.5 |
| Tetramethylthiourea | 0.75 |
| N-cyclohexyl-2-benzothiazolesulfenamide | 0.75 |

Example 9

In this example chloroprene Polymer C is used with three different accelerators. The compounding recipe is as follows:

| | Parts by Weight |
|---|---|
| Chloroprene Polymer C | 100 |
| Stearic acid | 0.5 |
| N-Phenyl-1-naphthylamine | 2 |
| Magnesia | 4 |
| Medium thermal black | 100 |
| Naphthenic oil | 10 |
| Paraffin | 1 |
| Tetraethylthiuram disulfide | 0.75 |
| Zinc oxide | 5 |
| Accelerator (as shown) | As Shown |

The results are tabulated below:

TABLE VI

| Compound of Example | 1 | 2 | 3 | TMTU (comparison) |
|---|---|---|---|---|
| Amount | 3.0 | 3.0 | 2.3 | 1 |
| Mooney scorch | | | | |
| Original (Unaged) | | | | |
| Minimum | 18.5 | 18.5 | 19 | 21 |
| Minutes to 10-point rise | 36.5 | 36 | 36 | 25.5 |
| Aged 2 weeks at 38°C. | | | | |
| Minimum | 19 | 20 | 20 | 28 |
| Minutes to 10-point rise | 30.5 | 33 | 33 | 16.5 |

TABLE VI-continued

| Compound of Example | 1 | 2 | 3 | TMTU (comparison) |
|---|---|---|---|---|
| Amount | 3.0 | 3.0 | 2.3 | 1 |
| Tensile properties (cured 25 min. at 153°C.) | | | | |
| $M_{300}$ | 1240 | 1200 | 1280 | 1480 |
| $T_B$ | 1470 | 1430 | 1420 | 1695 |
| $E_B$ | 445 | 455 | 355 | 390 |

Example 10

Example 5 is repeated except that the accelerator is the compound of Example 4, which is used in three different amounts. The results are shown in the following table.

TABLE VII

| Amount of accelerator | 1.2 | 2.4 | 3.6 |
|---|---|---|---|
| Mooney scorch | | | |
| Minimum | 22 | 21 | 19 |
| Points rise after 45 min. | 2 | 2 | 3 |
| Tensile properties (cured 25 min. at 153°C.) | | | |
| $M_{100}$ | 440 | 560 | 640 |
| $T_B$ | 2350 | 2730 | 2670 |
| $E_B$ | 345 | 325 | 310 |

I claim:
1. In the process of vulcanizing in the presence of magnesium oxide and zinc oxide an elastomer composition comprising as the elastomer a chloroprene polymer containing 0–60 weight percent of 2,3-dichloro-1,3-butadiene,
the improvement of using as vulcanization accelerator a polycarbamate represented by the following formula

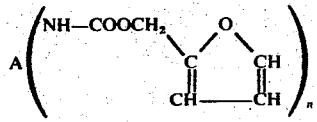

wherein A is 1,3-phenylene, 1,4-phenylene, 4,4'-methylenediphenylene, and polymethylene polyphenyl; and n is a positive number from 2 to 3;
provided that the aromatic rings in the A radical can be substituted with one or more $C_1$–$C_4$ alkyl groups;
the proportion of the polycarbamate being about 0.5–4 parts; the proportion of magnesium oxide being about 0.4–15 parts; and the proportion of zinc oxide being about 2–15 parts; all parts being by weight per 100 parts by weight of the polymer.

2. The improvement of claim 1, wherein the vulcanization is carried out at about 125°–220°C. during about two minutes to one hour.

3. The improvement of claim 1 wherein the polycarbamate's radical A is polymethylenepolyphenyl, and n is about 2.3–2.7.

4. The improvement of claim 1 wherein the polycarbamate's radical A is 2,4-tolylene, and $n$ is 2.

5. The improvement of claim 1 wherein the polycarbamate's radical A is a mixture of 2,4-tolylene and 2,6-tolylene, and $n$ is 2.

6. The improvement of claim 1 wherein the polycarbamate's radical A is 1,4-phenylene.

7. The improvement of claim 1 wherein the polycarbamate's radical A is 4,4'-methylenediphenylene.

8. The improvement of claim 2 wherein the chloroprene polymer is a homopolymer of chloroprene.

9. The improvement of claim 2 wherein the chloroprene polymer is a copolymer of chloroprene with 2,3-dichloro-1,3-butadiene.

10. An unvulcanized, vulcanizable elastomer composition in which the elastomer is a polymer of chloroprene containing 0–60 percent by weight of 2,3-dichloro-1,3-butadiene, said composition containing in addition to the elastomer 0.5–15 parts of magnesium oxide, 2–15 parts of zinc oxide, and 0.5–4 parts of a polycarbamate represented by the following formula:

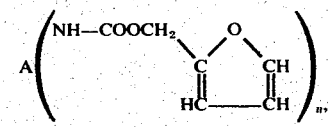

wherein A is 1,3-phenylene, 1,4-phenylene, 4,4'-methylene diphenylene, and polymethylene polyphenyl; and $n$ is a positive number from 2 to 3;
provided that the aromatic rings in the A radical can be substituted with one or more $C_1$–$C_4$ alkyl groups;
all parts being by weight per 100 parts by weight of the polymer.

11. A composition of claim 10 wherein the proportion of magnesium oxide is 1–4 parts, by weight per 100 parts by weight of the polymer.

12. A composition of claim 10 wherein the proportion of zinc oxide is about 5 parts by weight per 100 parts by weight of the polymer.

13. The composition of claim 10 wherein the chloroprene polymer is a homopolymer of chloroprene.

14. The composition of claim 10 wherein the chloroprene polymer is a copolymer of chloroprene and 2,3-dichloro-1,3-butadiene.

* * * * *